United States Patent [19]
Wei et al.

[11] Patent Number: 6,004,314
[45] Date of Patent: Dec. 21, 1999

[54] OPTICAL COHERENCE TOMOGRAPHY ASSISTED SURGICAL APPARATUS

[75] Inventors: Jay Wei, Fremont; Thomas Hellmuth, Danville, both of Calif.

[73] Assignee: Carl Zeiss, Inc., Thornwood, N.Y.

[21] Appl. No.: 08/832,598

[22] Filed: Mar. 31, 1997

Related U.S. Application Data

[63] Continuation of application No. 08/404,244, Mar. 15, 1995, abandoned, which is a continuation-in-part of application No. 08/292,433, Aug. 18, 1994, Pat. No. 5,493,109.

[51] Int. Cl.$^6$ .................................................... A61N 5/02
[52] U.S. Cl. .................................... 606/12; 606/2; 606/3; 606/13; 606/18
[58] Field of Search ....................... 606/2, 3–19

[56] References Cited

U.S. PATENT DOCUMENTS

| | | |
|---|---|---|
| 4,512,642 | 4/1985 | Ito et al. . |
| 4,669,466 | 6/1987 | L'Esperance ................................ 606/5 |
| 4,685,140 | 8/1987 | Mount, II . |
| 4,795,250 | 1/1989 | Nakamura et al. ...................... 351/212 |
| 4,931,630 | 6/1990 | Cohen et al. ......................... 250/201.3 |
| 4,994,058 | 2/1991 | Raven et al. . |
| 5,071,417 | 12/1991 | Sinofsky .................................. 606/12 |
| 5,098,426 | 3/1992 | Sklar et al. . |
| 5,263,951 | 11/1993 | Spears et al. ............................... 606/5 |
| 5,281,211 | 1/1994 | Parel et al. .................................. 606/5 |
| 5,288,987 | 2/1994 | Vry et al. .............................. 250/201.3 |
| 5,324,281 | 6/1994 | Muller ......................................... 606/5 |
| 5,336,216 | 8/1994 | Dewey ......................................... 606/4 |
| 5,359,417 | 10/1994 | Müller et al. . |
| 5,493,109 | 2/1996 | Wei et al. .................................. 606/10 |

FOREIGN PATENT DOCUMENTS

| | | | |
|---|---|---|---|
| WO 92/19930 | 12/1992 | WIPO .............................. G01B 9/02 |
| WO 93/16631 | 9/1993 | WIPO .............................. A61B 5/02 |

OTHER PUBLICATIONS

Therapeutic and Diagnostic Application of Lasers in Ophthalmology by K. P. Thompson, Q. S. Ren and and J–M Parel, *Proc. of the IEEE*, vol. 80, No. 6, Jun. 1992, pp. 838–859.

In vivo retinal imaging by optical coherence tomography by E. A. Swanson, J. A. Izatt, M. R. Hee, D. Huang, C. P. Lin, J. S. Schuman, C. A. Puliafito and J. G. Fujimoto, *Optics Lett.*, vol. 18, No. 21, Nov. 1, 1993, pp. 1864–1866.

New Equipment and Methods for Determining The Contour of the Human Cornea by M. G. Townsley, *Contacto*, 11(4), 1967, pp. 72–81.

Accuracy and Precision of Keratometry, Photokeratoscopy, and Corneal Modeling on Calibrated Steel; Balls by S. B. Hannush, S. L. Crawford, G. O. Waring III, M. C. Gemmill, M. J. Lynn, and A. Nizam in *Arch. Ophthalmol.*, vol. 107, Aug. 1989, pp. 1235–1239.

Optical Coherence Tomography by Huang et al., published in *Science*, 254, Nov. 22, 1991, pp. 1178–1181.

Intraoperative raster photogrammetry—the PAR Corneal Topography System by M. W. Berlin, *J. Cataract Refract Surg*, vol. 19, Supplement, 1993, pp. 188–192.

Micron–Resolution Imaging of the Anterior Eye in Vivo with Optical Coherence Tomography by J. A. Izatt, M. R. Hee, E. A. Swanson, C. P. Lin, D. Huang, J. S. Schuman, C. A. Puliafito,and J. G. Fujimoto, 1994, pp. 1–24.

Micron–Resolution Ranging of Cornea Anterior Chamber by Optical Reflectometry by D. Huang, J. Wang, C. P. Lin, C. A. Puliafito, and J. G. Fujimoto, *Lasers in Surgery and Medicine*, vol. 11, 1991, pp. 419–425.

Measurement of corneal thickness by low–coherence interferometry by C. K. Hitzenberger, *Applied Optics*, vol. 31, No. 31, Nov. 1, 1992, pp. 6637–6642.

*Primary Examiner*—David M. Shay
*Attorney, Agent, or Firm*—Michael B. Einschlag

[57] ABSTRACT

Ophthalmologic surgical microscope which is combined internally with an optical coherence tomography ("OCT") apparatus wherein auto-focusing is provided by driving a motorized internal focusing lens of the ophthalmologic surgical microscope with a signal output from the OCT apparatus. An embodiment of the inventive ophthalmologic surgical microscope includes: (a) an optical coherence tomography ("OCT") apparatus; (b) a beamcombiner for internally coupling output from the OCT apparatus into the ophthalmologic surgical microscope; and (c) a motor for moving an internal focusing lens of the ophthalmologic surgical microscope in response to a signal from the OCT apparatus, whereby the ophthalmologic surgical microscope is auto-focused.

49 Claims, 5 Drawing Sheets

OPTICAL COHERENCE TOMOGRAPHY ASSISTED SURGICAL APPARATUS

CROSS-REFERENCE TO RELATED APPLICATION

This is a continuation of Ser. No. 08/404,244 filed on Mar. 15, 1995, which is a continuation-in-part of a patent application having Ser. No. 08/292,433 which was filed on Aug. 18, 1994, now U.S. Pat. No. 5,493,109.

TECHNICAL FIELD OF THE INVENTION

The present invention relates to optical coherence tomography ("OCT") assisted surgical apparatus such as: (a) an ophthalmologic surgical microscope which includes an OCT unit for auto-focusing on the posterior intraocular lens capsule for use, for example, in cataract surgery and for performing in-line corneal topography measurements for use, for example, in refractive surgery and (b) a laser surgical apparatus which includes an OCT unit for controlling laser parameters such as exposure time, focus size, and power.

BACKGROUND OF THE INVENTION

As is well known, cataract surgery is an ophthalmologic surgical procedure for removing an opaque intraocular lens from an eye. In accordance with this surgical procedure, after the intraocular lens is removed, an artificial intraocular lens needs to be implanted to recover the patient's vision. It is desirable for an ophthalmologic surgical microscope that is used during the surgical procedure to have a capability of auto-focusing on the intraocular lens capsule during the surgical procedure, which capability is especially important after a majority of the opaque intraocular lens has been removed. After a majority of the opaque intraocular lens has been removed, small amounts of cataract residue may remain on the optically transparent intraocular lens capsule—because the intraocular lens capsule is transparent, such residue is difficult to see. As is known, it is important to completely remove such residue because any residue left on the intraocular lens capsule will serve as a nucleus of a new cataract. Present apparatus for auto-focusing an ophthalmologic surgical microscope, such as a prior art apparatus disclosed in U.S. Pat. No. 5,288,987 issued Feb. 22, 1994, are based on detecting and measuring the intensity of light scattered from an object. However, such apparatus for auto-focusing are disadvantageous because it is difficult to focus on an optically transparent medium such as the posterior intraocular lens capsule since reflection therefrom is specular and weak.

In light of the above, there is a need in the art for an ophthalmologic surgical microscope which can auto-focus on the posterior intraocular lens capsule for use in cataract surgery.

As is well known, refractive surgery is a surgical procedure that has, as its primary objective, correction of an ametropia by making incisions in a cornea to change the refractive power of the cornea. Surgical manipulation of corneal shape requires an accurate and precise method of measuring anterior corneal curvature from apex to limbus. At present, measurement of curvature of the center of the cornea is commonly made using a keratometer and, for more precise measurements of corneal topography, it is common to utilize photokeratoscopy or videokeratoscopy.

Current corneal topography measurement apparatus are mostly Placido-disc-based videokeratoscopes. In such an apparatus, a series of concentric rings are configured on a cone-shaped housing so that an image reflected from the cornea is virtually flat in space. Then, the configuration of the rings is analyzed to determine the corneal topography. A prior art apparatus of this type has been described in an article entitled "New Equipment and Methods for Determining The Contour of the Human Cornea" by M. G. Townsley, Contacto, 11(4), 1967, pp. 72–81. Such videokeratoscopes have the following disadvantages: (a) due to the small radius of the cornea (~8 mm), a limited number of rings can be resolved on the cornea (normally, the contour which can be measured is restricted to an area which ranges from 0.8 to 11 mm in diameter on the cornea); (b) no information can be obtained between the rings; and (c) due to use of rings, in-line measurement is very difficult when used in conjunction with an ophthalmologic surgical microscope. An article entitled "Accuracy and Precision of Keratometry, Photokeratoscopy, and Corneal Modeling on Calibrated Steel; Balls" by S. B. Hannush, S. L. Crawford, G. 0. Waring III, M. C. Gemmill, M. J. Lynn, and A. Nizam in Arch. Ophthalmol., Vol. 107, August 1989, pp. 1235–1239 provides a comparison of these prior art methods and apparatus.

Another corneal topography measurement apparatus has been developed recently by PAR Microsystem Co. The apparatus utilizes raster photogrammetry to measure a corneal topography. In this apparatus, a grid pattern is projected onto the cornea. The grid pattern is then viewed and imaged from an offset angle. Finally, corneal elevation at each of the discrete points in the grid pattern are calculated using the image of the projected grid pattern, and information relating to its geometry. This apparatus is described in an article entitled "Intraoperative raster photogrammetry—the PAR Corneal Topography System" by M. W. Berlin, J. Cataract Refract Surg, Vol. 19, Supplement, 1993, pp. 188–192. Corneal topography measurements suffer in this apparatus because only a limited number of points in the image of the projected grid pattern can be resolved by the image optics.

As is further known, since a posterior corneal surface contributes about −14% of total corneal refractive power, in some cases, an anterior corneal topography, by itself, does not provide sufficient information for use in a refractive surgical procedure. For that reason, it becomes even more important to obtain corneal topography measurements with a precision that cannot be provided by current corneal topography measurement apparatus.

In light of the above, there is a need in the art for an ophthalmologic surgical microscope which can perform in-line, corneal topography measurements for use in refractive surgical procedures.

Recently, a new ophthalmic measurement apparatus, an optical coherence tomography ("OCT") apparatus, has been disclosed which has advantages over the above-described prior art ophthalmic measurement apparatus. An OCT apparatus uses a short coherence light source for range measurements based on the principle of white light interferometry. OCT has been proposed recently for use in several ophthalmologic applications. For example, such proposals have been made in a preprint of an article which has been submitted for publication entitled "Micron-Resolution Imaging of the Anterior Eye in Vivo with Optical Coherence Tomography" by J. A. Izatt, M. R. Hee, E. A. Swanson, C. P. Lin, D. Huang, J. S. Schuman, C. A. Puliafito, and J. G. Fujimoto, 1994, pp. 1–24. The preprint discloses an OCT apparatus which utilizes optical fiber technology and a superluminescent laser diode source, which OCT apparatus is interfaced with a slitlamp biomicroscope for imaging intraocular structures with a spatial resolution of 10–20 µm.

The preprint discloses the use of the OCT apparatus to provide direct, micron-resolution measurements of (a) ocular profile dimensions, optical scattering, and structure in the cornea; (b) the anterior angle region; (c) the iris; and (d) the crystalline lens. The preprint further discloses the use of the OCT apparatus to measure: (a) anterior chamber depth, defined as a distance, along the visual axis, from the posterior corneal surface to the lens anterior capsule; (b) radius of curvature of the posterior and anterior surfaces of the cornea; (c) corneal refractive power; and (d) corneal dimensions such as thickness. The preprint still further discloses that the OCT apparatus, using an inexpensive diode laser source and a fiber optic implementation, is compatible with existing ophthalmic instrumentation. Finally, the preprint makes the following suggestions for potential clinical applications of OCT: (a) providing cross-sectional images of the entire anterior chamber for use in elucidating pathologies of the cornea, anterior angle region, and iris and for use in identifying and monitoring intraocular masses or tumors; (b) measuring anterior chamber depth, corneal curvature, and corneal refractive power; and (c) providing high resolution images showing corneal thickness variations and the distribution of scattering in corneal stroma for quantitative analysis of corneal pathologies.

As is well known, lasers are used in eye surgery for various applications, of which, perhaps the most important are photocoagulation of the retina and photoablation of the cornea. In such applications, laser radiation interacts with ocular tissue and causes structural and topological changes of the tissue. Such applications typically entail monitoring such tissue changes visually on a video monitor by means of a CCD microchip interface or through a binocular eye piece with an ophthalmologic surgery biomicroscope. However, the CCD image of the prior art is limited for two basic reasons. The first reason the CCD image of the prior art is limited is that the CCD image only provides an image of tissue surface. For laser treatment of macular holes, for example, although there is a need to limit tissue coagulation to a well defined area to avoid unnecessary damage of visual functions, there is also a need to limit tissue coagulation in depth to avoid bleeding of the highly perfused coroidal layer. Another example of the need to limit tissue changes in depth is the need to avoid damage of the endothelium layer of the cornea during laser ablation for photorefractive surgery. The second reason the CCD image of the prior art is limited is that it does not provide a quantitative method for controlling tissue change based on laser power, exposure, and spot size.

In light of the above, there is a need for an apparatus for use in laser treatment for controlling the extent of tissue change during the laser treatment and for controlling the tissue change based on laser power, exposure, and spot size.

SUMMARY OF THE INVENTION

An embodiment of the present invention comprises an ophthalmologic surgical microscope which is combined internally with an optical coherence tomography ("OCT") apparatus wherein auto-focusing is provided by driving a motorized internal focusing lens of the ophthalmologic surgical microscope with a signal output from the OCT apparatus. In accordance with one embodiment of the present invention, whenever a particular object in the field of view is interesting, for example, the posterior lens capsule, the OCT apparatus scans the anterior chamber of the eye, along the longitudinal axis of the eye, to provide location information relating to the particular object. Then, the OCT apparatus outputs a location signal to drive the motorized internal focusing lens to autofocus the ophthalmologic surgical microscope on the particular object.

In accordance with another embodiment of the present invention, in-line corneal tomography measurements of the anterior chamber are obtained by using a scanning apparatus, for example, a scanning apparatus comprised of two scanning motors, to provide a raster transverse OCT scan of the cornea, in conjunction with a longitudinal OCT scan. The results of the scans are analyzed by a computer to provide the following data: (a) anterior corneal surface contours, (b) posterior corneal surface contours, and (c) the thickness of the cornea. As one can readily appreciate such contours are three-dimensional contours. These data are used to provide in-line, on-line monitoring of corneal refractive power during a refractive surgical procedure.

In accordance with the present invention, embodiments of the ophthalmologic surgical microscope provide eye pieces and a CCD camera for direct viewing during the surgical procedure. Advantageously, since the OCT apparatus is combined with the ophthalmologic surgical microscope internally, the working distance of the microscope objective lens is preserved.

An embodiment of another aspect of the present invention comprises a laser delivery system which is combined with an OCT apparatus wherein the extent of tissue change during laser treatment is monitored and controlled by analyzing output from the OCT apparatus to control the laser delivery system.

BRIEF DESCRIPTION OF THE FIGURE

Components which are the same in the various figures have been designated by the same numerals for ease of understanding.

DETAILED DESCRIPTION

Figure 1:
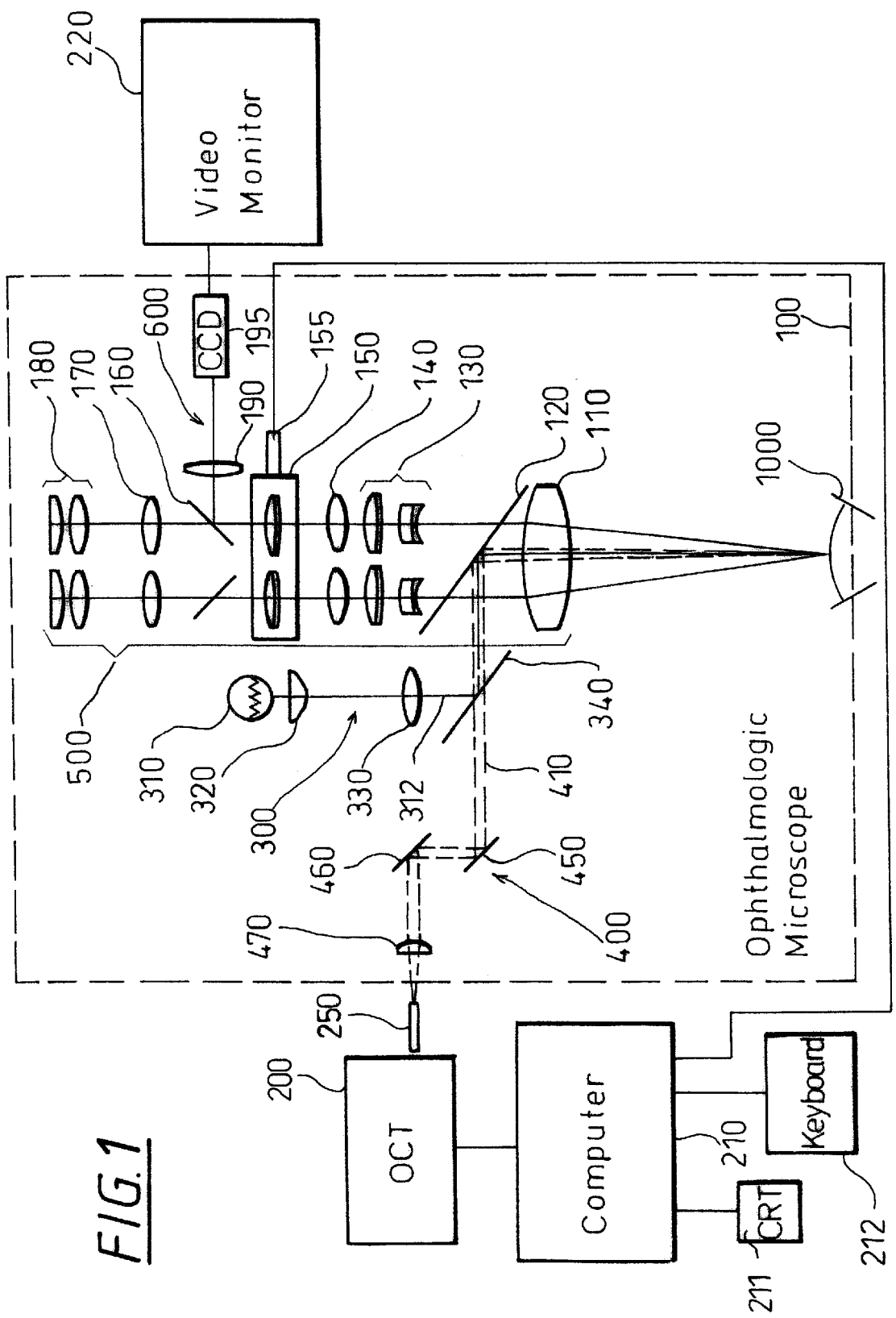
FIG. 1 shows, in pictorial form, an embodiment of the present invention which comprises an ophthalmologic surgical microscope and an optical coherence tomography ("OCT") apparatus.

FIG. 1 shows, in pictorial form, an embodiment of the present invention which comprises ophthalmologic surgical microscope 100, optical coherence tomography apparatus 200 ("OCT 200"), and video imaging unit 220. As shown in FIG. 1, ophthalmologic surgical microscope 100 is comprised of objective lens 110 which has a long working distance (~200 mm) for focusing on patient's eye 1000 during a surgical procedure. Beamcombiner 120 directs illumination radiation 310 from illumination path 300 and OCT radiation 410 from OCT path 400 toward objective lens 110. As is shown in FIG. 1, beamcombiner 120 is beamsplitter. As is shown in FIG. 1, ophthalmologic surgical microscope 100 further comprises optical magnification changer 130 which is set to a condition suitable for performing a particular surgical procedure (typically there are a number of groups of lenses arranged on a drum for providing varying magnifications such as, for example, 5×, 12×, 20×, and so forth). Radiation impinging upon optical magnification changer 130 is collimated.

Ophthalmologic surgical microscope 100 further comprises: (a) relay lenses 140 which take collimated radiation output from optical magnification changer 130 and form an intermediate image of an object, for example, eye 1000; and (b) internal focusing lenses 150 which are used to focus on the intermediate image of the object formed by relay lenses 140 and provide a collimated beam (internal focusing lenses 150 move up and down along viewing path 500 to provide an opportunity for internal focus adjustment).

After passing through internal focusing lenses 150, radiation is collimated and beamsplitter 160 couples a portion of the collimated radiation into optical path 600 for obtaining a video image. The video image is obtained by use of video lens 190, CCD camera 195, and video monitor 220. As those of ordinary skill in the art can readily appreciate, although the use of a single CCD camera is shown, it is within the spirit of the present invention that embodiments may be fabricated utilizing two beamsplitters, i.e., beamsplitter 160 and a similarly placed beamsplitter, to provide stereoscopic viewing through two CCD cameras.

Lastly, tube lenses 170 focus collimated radiation passed through beamsplitters 160 at an object plane of eye pieces 180. Eye pieces 180 then provide collimated output which is focused by a viewer's eyes. Since the above-described viewing path 500 is binocular, stereoscopic viewing can be obtained.

As shown in FIG. 1, illumination path 300 is comprised of: (a) incandescent light source 310; (b) condenser lens 320 for collecting radiation output from light source 310; and (c) image lens 330 for filling the entrance pupil of objective lens 110 with the filament of incandescent light source 310. Beamcombiner 340 combines OCT beam 410 with illumination radiation 310 from illumination path 300. In a preferred embodiment, beamcombiner 340 is a cold mirror beamsplitter, i.e., a mirror which reflects radiation at lower wavelengths, for example, wavelengths less than about 700 nm, and transmits radiation at higher wavelengths, for example, wavelengths higher than about 700 nm.

Figure 2:
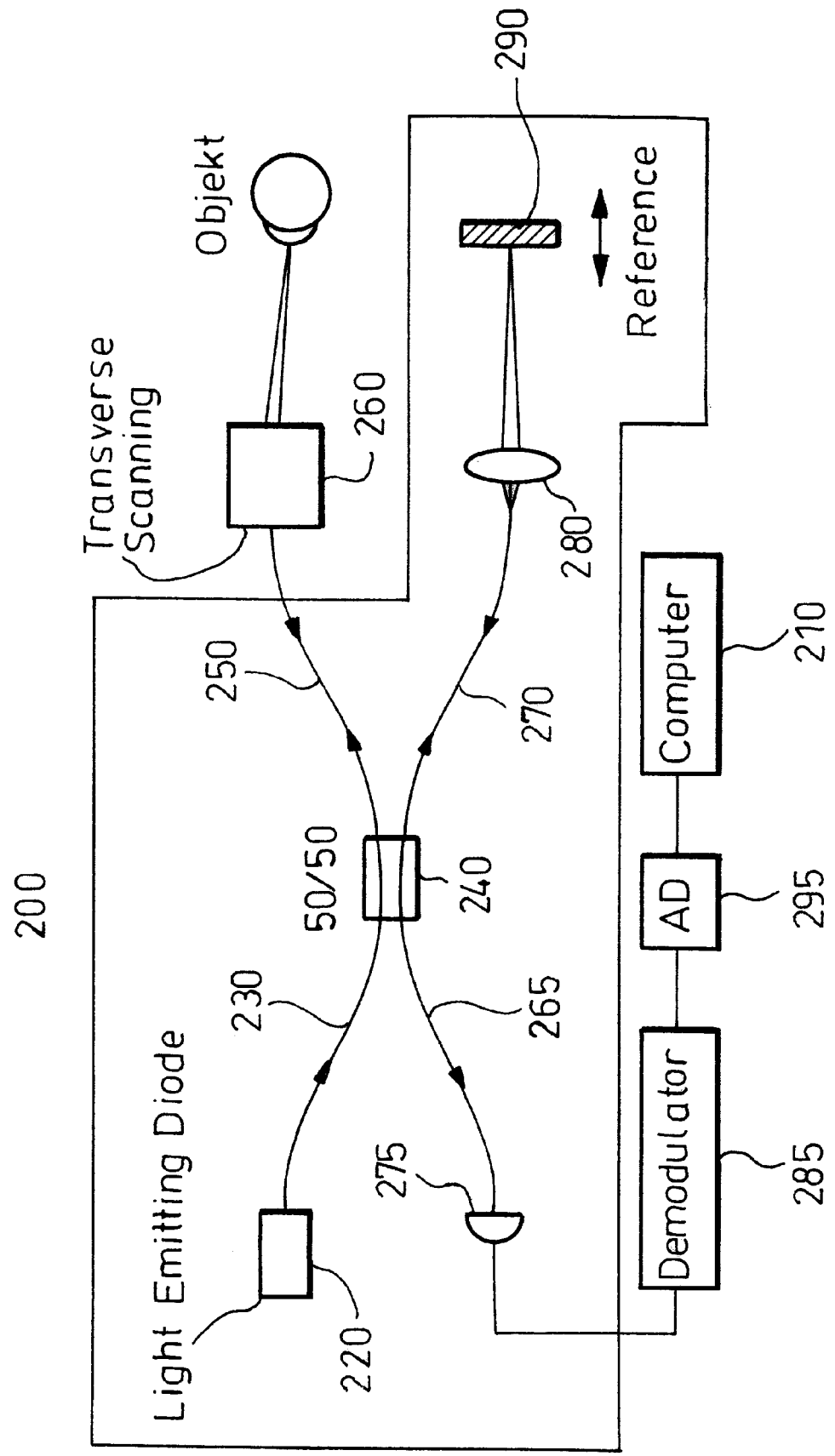
FIG. 2 shows, in pictorial form, a fiber optic embodiment of the OCT apparatus shown in FIG. 1.

FIG. 2 shows, in pictorial form, a fiber optic embodiment of OCT apparatus 200. As shown in FIG. 2, OCT apparatus 200 comprises CW radiation source 220, for example, a superluminescent laser diode having an output centered substantially at 850 nm. Output from source 220 is coupled into optical fiber 230 and is separated into two beams by 50/50 coupler 240. The output from 50/50 coupler 240 is coupled into optical fibers 250 and 270, respectively. The output from fiber 270 is imaged by lens 280 onto reference mirror 290 and output from fiber 250 is directed to transverse scanning mechanism 260. The output from transverse scanning mechanism 260 is directed to impinge upon an object in a manner to be described in detail below. Then, radiation reflected from the object is coupled back into fiber 250 and superimposed by 50/50 coupler 240 with radiation reflected from reference mirror 290 and coupled back into fiber 270. Superimposed radiation output from 50/50 coupler 240 is coupled into fiber 265. As is known, there is interference between radiation reflected from the object and radiation reflected from reference mirror 290 if the optical path difference is smaller than the coherence length of radiation source 220. Reference mirror 290 is moved with a substantially constant velocity by means which are well known to those of ordinary skill in the art (not shown) and, as a result, the interference is detected as a periodic variation of a detector signal obtained by photodetector 275, the periodic variation having a frequency equal to a Doppler shift frequency which is introduced by moving reference mirror 290 with the constant velocity. The output from photodetector 275 is demodulated by demodulator 285, the demodulated output from demodulator 285 is converted to a digital signal by analog-to-digital converter 295 (A/D 295), and the output from A/D 295 is applied as input to computer 210 for analysis. The interference signal vanishes as soon as the optical path difference between radiation reflected from the object and radiation reflected from reference mirror 290 becomes larger than the coherence length of source 220.

As shown in FIG. 1, the output from OCT apparatus 200 over fiber 250 is coupled into OCT path 400, which OCT path 400 includes a transverse scanning mechanism which will described below. As described above, in the embodiment shown in FIG. 1, OCT beam 410 has a wavelength centered about 850 nm and beamsplitter 120 is coated with a dichroic coating so that radiation from OCT path 400 can be continuously scanned during a surgical procedure without interruption of viewing by ophthalmologic surgical microscope 100.

Figure 4:
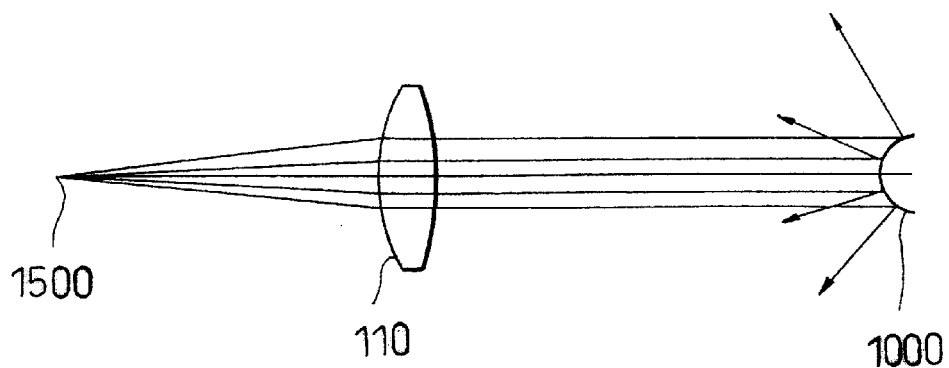
FIG. 4 shows, in pictorial form, the chief rays of the OCT beam between the scanning mirrors and the eye for the embodiment shown in FIG. 1.

In accordance with the present invention, there are two configurations utilized to provide transverse scanning. In the first configuration used to provide transverse scanning, as shown in FIG. 1, scanning mirrors 450 and 460 are orthogonally mounted, galvanometer driven scanning mirrors which are mounted on a pair of motors (not shown) and lens 470 collimates radiation output from fiber 250. The scanning motors are operated under the control of computer 210 in a manner which is well known to those of ordinary skill in the art. In the first configuration, scanning mirrors 450 and 460 are located close to the back focus of objective lens 110. FIG. 4 shows, in pictorial form, the chief rays of OCT beam 410 between scanning mirrors 450 and 460 and eye 1000 in the first configuration. As shown in FIG. 4, back focus 1500 of objective lens 110 is close to scanning mirrors 450 and 460 and the chief rays of OCT beam 410 are parallel to the optical axis in object space, i.e., the region between objective lens 110 and eye 1000. As one can readily see from FIG. 4, radiation reflected from the outer rim of the cornea of eye 1000 will be directed away from a return path to OCT apparatus 200 due to the large angle of incidence of the radiation on the cornea.

Figure 3:
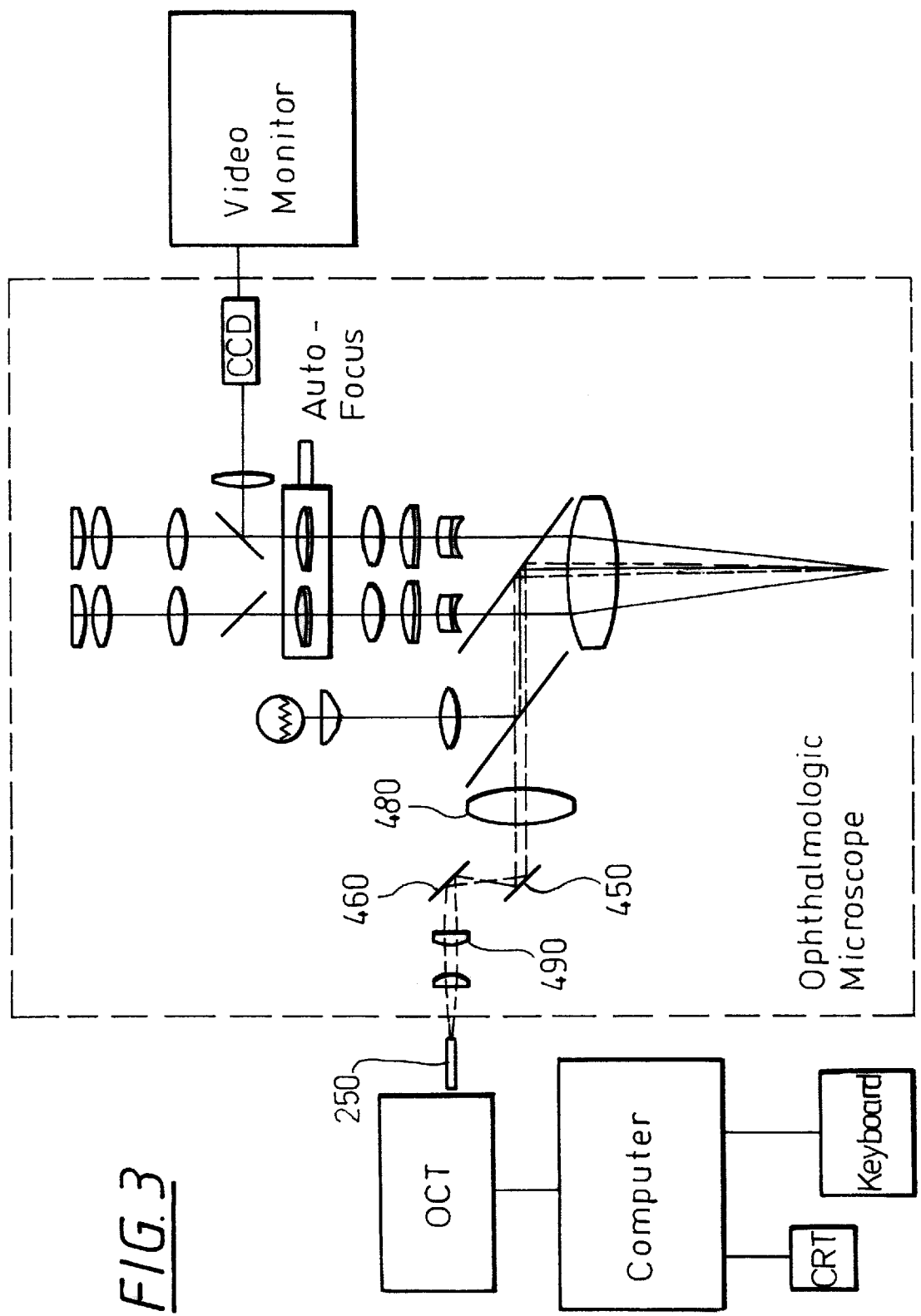
FIG. 3 shows, in pictorial form, a preferred embodiment of the present invention which comprises an ophthalmologic surgical microscope and an OCT apparatus.

The second configuration used to provide transverse scanning is illustrated in FIG. 3. As shown in FIG. 3, relay lens 490 is used to transfer the OCT point source from fiber 250 to an intermediate image which is located between scanning mirrors 450 and 460 and scanning mirrors 450 and 460 are located very close to the back focus of scanning lens 480.

Figure 5:
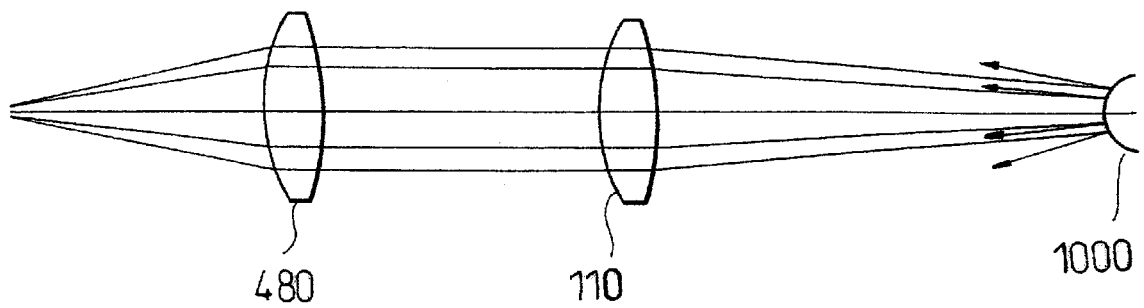
FIG. 5 shows, in pictorial form, the chief rays of the OCT beam between the scanning mirrors and the eye for the embodiment shown in FIG. 3.

FIG. 5 shows, in pictorial form, the chief rays of OCT beam 410 between scanning mirrors 450 and 460 and eye 1000 in the second configuration. As shown in FIG. 5, the chief rays of the scanning beam are parallel in relay space, i.e., the space between scanning lens 480 and objective lens 100 and the chief rays are focused close to the center of curvature of the cornea of eye 1000. Since OCT beam 410 is focused at the center of curvature of the cornea, it is normal to the surface thereof and the reflected beam is retroreflected into the return path. As a result, in the second case, the maximum signal strength is obtained everywhere on the cornea and the embodiment shown in FIG. 3 is the preferred embodiment of the present invention.

In accordance with a first aspect of the present invention, OCT unit 200, in accordance with instructions from computer 210, scans the anterior chamber of eye 1000, along the longitudinal axis of the eye, in a manner known in the art to provide location information relating to a particular object, for example, the posterior lens capsule. This object is one of several layers in the anterior chamber of the eye. Each maximum of the OCT signal reflected from these layers corresponds to a specific layer. The reference mirror scans a distance of the order of several centimeters corresponding to the focusing image of internal focusing lens 150 in the object space of the surgical microscope.

The zero positon of the reference mirror corresponds to a nominal distance of the object plane from objective lens 110. Computer 210 detects each of the OCT signal maxima and registers the respective positions of the reference mirror. This information gives the distance of each layer from objective lens 110.

Each maximum corresponds to a specific layer. The number of layers is unique for the specific circumstances of cataract surgery. The number of the layer of interest can be determined by the operator and is part of the initial configuration of the computer program. Usually, the posterior lens capsule is the layer of interest.

Then, computer 210 positions internal focusing lenses 150 (by sending an appropriate signal to motor 155) so that the corresponding focal plane of the surgical microscope, depending on the position of internal focusing lenses 150, is at the position of the posterior lens capsule identified with the said procedure.

In addition, the output from computer 210 may be displayed on CRT 211 wherein various features obtained by the OCT longitudinal scan are made apparent by a display, for example, of signal strength as a function of location. Since the position of the posterior ocular lens is well known, it can readily be identified by a trained observer. Then, user input to computer 210 by means, for example, of keyboard 212 and/or a mouse (not shown), is used to specify a range of locations of the longitudinal scan to use for autofocusing. In response to the user input, computer 210 chooses a location which produces a signal strength maximum within the specified range of locations and determines an appropriate position of internal focusing lens 150 to achieve proper focus on the location providing the signal strength maximum. Then, computer 210 sends an appropriate signal to motor 155 to move internal focusing lens 150 to the appropriate position.

In accordance with a second aspect of the present invention, OCT unit 200 and scanning mirrors 450 and 460, in accordance with instructions from computer 210, provide a raster, transverse OCT scan of the cornea in conjunction with a longitudinal OCT scan, all in a manner known in the art. The results are analyzed by computer 210 to obtain corneal topography measurements such as: (a) anterior corneal surface contours, (b) posterior corneal surface contours, and (c) the thickness of the cornea. As one can readily appreciate such contours are three-dimensional contours. These data are used to provide on-line monitoring of corneal refractive power during a refractive surgical procedure. In one embodiment of this aspect of the present invention, thresholds are input to computer 210 for the purpose of identifying signals maxima corresponding to predetermined surfaces in the chamber of the eye. Then, computer 210 makes a correspondence between signals having levels above the maxima with the predetermined surfaces and captures the spatial coordinates of the surfaces in space from the longitudinal scan position and from the position of the OCT beam in the raster scan. These values in space are stored in computer 210. The thickness of the cornea is determined from the spatial difference between signal peaks produced by the posterior and anterior corneal surface during a longitudinal scan and the well known optical properties of the cornea, such as, for example, index of refraction. When the raster scan is completed, computer 210 performs a fit of the spatial coordinates of the surfaces to provide posterior and anterior corneal surface contours. As is well known to those of ordinary skill in the art, the surfaces of the cornea are not spherical and, as a result, the surfaces may be described by a set of curvatures, which set will be referred to as a curvature distribution. The surface contours are utilized to determine measures of the curvatures in the curvature distribution of the posterior and anterior surfaces of the cornea and, from them, a measure of corneal refractive power.

Figure 6:
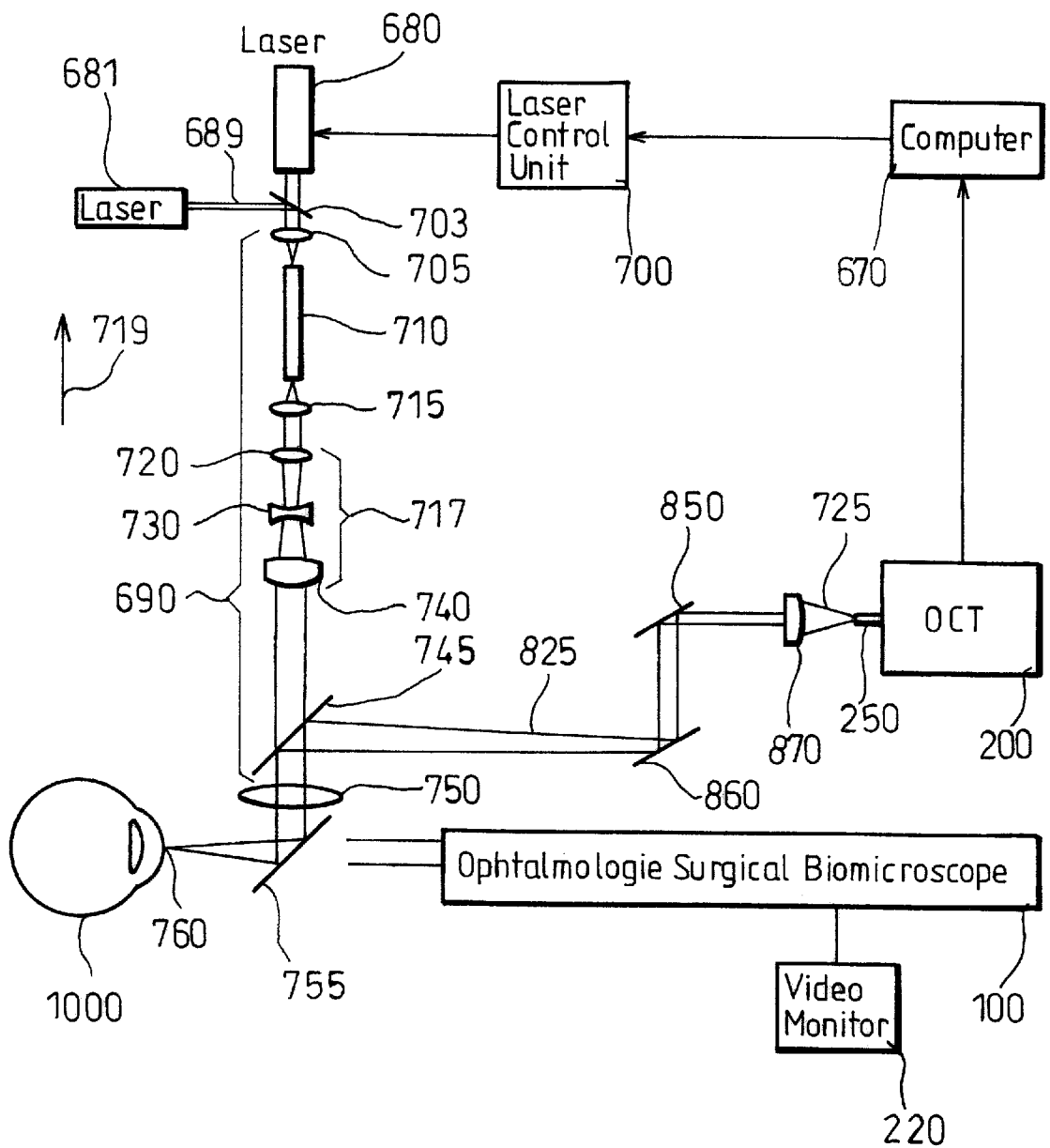
FIG. 6 shows, in pictorial form, an embodiment of the present invention for monitoring and controlling the extent of tissue change during laser treatment.

FIG. 6 shows, in pictorial form, an embodiment of the present invention which comprises optical coherence tomography ("OCT") apparatus 200, computer 670, treatment laser 680, aiming laser 681, laser delivery optics 690, laser control unit 700, ophthalmologic surgical biomicroscope 100, and video monitor 220. As shown in FIG. 6, output from treatment laser 680 passes through dichroic beamsplitter 703 and is focused by lens system 705 into lightguide 710 and output from aiming laser 681 is reflected by dichroic beamsplitter 703 and is focused by lens system 705 into lightguide 710. Embodiments of treatment laser 680 for use in, for example, photocoagulation and photoablation, are well known in the art and embodiments of aiming laser 681 are also well known in the art. For example, one well known laser used to embody aiming laser 681 is a He—Ne laser.

The output from lightguide 710 is converted into a substantially parallel laser beam by collimating lens 715, which substantially parallel laser beam is applied as input to parfocal system 717. As shown in FIG. 6, parfocal system 717 is comprised of converging lens 720, diverging lens 730, and converging lens 740. Lens 720 and 730 are movable along the axis of laser delivery optics 690. Apparatus for moving lenses 720 and 730 along the axis of laser delivery optics 690 are well known in the art and are not shown for clarity and for ease of understanding the present invention. The direction of the axis of laser delivery optics 690 is shown by arrow 719 and will be referred to below as the z-axis. As is well known in the art, the output from parfocal system 717 is a substantially parallel beam having a variable beam diameter, the size of the beam diameter being determined by the positions of lenses 720 and 730 along the z-axis, i.e., the axis of laser delivery optics 690.

As shown in FIG. 6, the output from parfocal system 717 passes through beamcombiner 745 and is applied as input to micromanipulator lens 750. The output from micromanipulator lens 750 is directed by beamdirector 755 to laser focus 760 on eye 1000. FIG. 6 shows the laser beam being focused onto the cornea of eye 1000. However, it should be clear to those of ordinary skill in the art that the laser beam can also be focused onto the retina with the same configuration by, for example, using a contact lens which is pressed against the cornea of the patient's eye. The purpose of the contact lens is to neutralize the refractive power of the cornea. In this case, the working distance between the eye and the apparatus is adjusted so that the laser beam is focused onto the retina.

Beamcombiner 745 combines laser radiation output from parfocal system 717 with radiation from OCT beam 725 which is output from OCT apparatus 200. In a preferred embodiment, beamcombiner 745 is a beamsplitter which transmits laser radiation at wavelengths of the output from treatment laser 680 and aiming laser 681 and reflects radiation at wavelengths of OCT beam 725. In the preferred embodiment, beamdirector 755 is a mirror or a reflecting prism which is located between the two observation paths of ophthalmologic surgical biomicroscope 100. Micromanipulator lens 750 is movable in a plane which is perpendicular to the z-axis, which plane will be referred to below as the x-y plane. Apparatus for moving micromanipulator lens in the x-y plane are well known in the art and are not shown for clarity and for ease of understanding the present invention.

As shown in FIG. 6, OCT beam 725 is output from fiber 250 of OCT apparatus 200 and is collimated by lens 870. The collimated output from lens 870 impinges upon scanning mirrors 850 and 860 which are orthogonally mounted, galvanometer driven scanning mirrors. Scanning mirrors 850 and 860 are mounted on a pair of motors (not shown) which are operated under the control of computer 670 in a manner which is well known to those of ordinary skill in the art to provide transverse scanning of OCT beam 725. OCT beam 825 which emerges from scanning mirrors 850 and 860 is directed towards beamcombiner 745. In accordance with the present invention, scanning mirrors 850 and 860 are located substantially at the back focal plane of micromanipulator lens 750.

Scanning mirrors 850 and 860 are driven with a sawtooth profiled voltage function in a manner which is well known to those of ordinary skill in the art. When the phase and frequency of the respective driver voltages are equal, the resulting scan pattern is a linear scan. Thus, the linear scan (produced by scanning mirrors 850 and 860) combines with an OCT scan in a longitudinal direction into eye 1000 (produced by movement of reference mirror 290 shown in FIG. 2) to provide an OCT scan in a plane. The amplitudes of each sawtooth profile can be individually adjusted, in a manner which is well known to those of ordinary skill in the art, to change the orientation of the linear scan and, hence, the orientation of the plane of the OCT scan. The orientation of the linear scan and, hence, the orientation of the plane, are determined by the ratio of the amplitudes of each sawtooth profile. Thus, in accordance with the present invention, the plane of the OCT scan can be rotated (the z-axis is the axis of rotation) by varying the ratio of the amplitudes.

In the apparatus shown in FIG. 6, the principal rays of OCT beam 825 are in the same plane as the laser beam emerging from laser delivery system 690. Thus, OCT beam 825 is focused in the same focal plane as the beams from treatment laser 680 and aiming laser 681. In addition, OCT beam 825 moves when micromanipulator lens 750 is moved in the x-y direction. As a result, OCT beam 825 always scans transversely across laser focus 760 in the object plane and scans transversely across laser focus 760 symmetrically, i.e., the length of the portions of the transverse scan on either side of laser focus 760 are of equal length.

Radiation from OCT beam 825 is backscattered from eye 1000 and is coupled back to OCT apparatus 200. As described above with respect to FIG. 2, an OCT signal is generated by OCT apparatus 200 and is sent to computer 670 for analysis. Further, radiation from aiming laser 681 is reflected from eye 1000 through beamdirector 755 and into ophthalmologic surgical biomicroscope 100. Finally, video monitor 220 provides an image which is used to position laser focus 760 by changing the position of micromanipulator lens 750. The apparatus shown in FIG. 6 may also include illumination optics to provide an image of eye 1000 for viewing in conjunction with the position of laser focus 760 on video monitor 220. However, such illumination optics has been described above and is omitted here for sake of clarity and ease of understanding the present invention.

The following describes the analysis performed by computer 670 to control the operation of treatment laser 680. The amplitude of back scattered radiation from OCT beam 825 is different for laser-treated tissue and for untreated surrounding tissue. In fact, experimental studies show that the amplitude of such back scattered radiation is higher for laser-treated tissue than it is for untreated surrounding tissue and this fact is used to identify laser-treated tissue. The reflectivity of laser-treated tissue and untreated tissue is determined empirically as a function of, for example, laser power and exposure time. These data are utilized to develop reference threshold levels for use in the analysis. For example, an amplitude having a value above the reference threshold level is deemed to have been received from laser-treated tissue and an amplitude having a value below the reference threshold level is deemed to have been received from untreated tissue. As those of ordinary skill in the art understand, the effects of noise and small movements of the eye must be taken into account when determining the reference threshold levels. These reference threshold levels are stored in computer 670. As one can readily appreciate, the reference threshold levels may be a function of the type of tissue involved and/or the laser power and/or the exposure time. However, for purposes of understanding the present invention, we will assume that there is a single reference threshold level. With the following explanation, it should be clear to those of ordinary skill in the art how embodiments may be fabricated to take into account more complex variations of the reference threshold level.

In accordance with the present invention, computer 670 activates OCT apparatus 200 and scanning mirrors 850 and 860 to provide an OCT scan of a portion of eye 1000. As was described above, scanning mirrors 850 and 860 produce a linear, transverse OCT scan and, at predetermined points in the linear, transverse OCT scan, OCT radiation reflected from all scatterers in the path of OCT radiation 825, along a longitudinal direction into eye 1000, is compared with radiation from a reference path whose optical length is varied periodically and which optical length is accurately known (see the description of OCT given above in conjunction with FIG. 2). As was described above, an OCT output signal is generated only when the optical length of the path of OCT radiation reflected from a feature of eye 1000 is equal to the optical length of the reference path, to within the OCT radiation temporal coherence length. In accordance with the present invention, amplitude information is obtained for reflected OCT radiation, as a function of depth along a longitudinal direction into eye 1000, at each of the predetermined points in the linear, transverse scan: Thus, after the OCT scan, computer 670 has collected data which comprises amplitude information over a plane (referred to below as a transverse plane), the transverse plane extending symmetrically about laser focus 760 and along the longitudinal direction into eye 1000. The data are analyzed by computer 670 to determine the area of the laser-treated tissue within the transverse plane. The area is compared with information regarding a desired clinical effect in a predetermined regimen of treatment, which information has been input to computer 670, for example, by a physician. Computer 670 then determines whether further exposure is warranted to achieve the desired clinical effect or whether the desired clinical effect has been achieved. Further, computer 670 interacts with treatment laser 680 by means of laser control unit 700 to turn off treatment laser 680 or to change the exposure time. Still further, computer 670 can indicate the need to change the spot size and can provide parameters for positioning of lenses 720 and 730 to achieve a desired spot size on a display which is a part of computer 670 so that an operator can position lenses 720 and 730 appropriately. Alternatively, lenses 720 and 730 can be mounted on motors (not shown), for example, stepper motors, and computer 670 can cause lenses 720 and 730 to be moved to provide the desired spot size by direct interaction with the motors in a manner which is well known to those of ordinary skill in the art. Another embodiment of the analysis is carried out by setting the reference threshold level to be a predetermined fraction of the maximum amplitude within the OCT image. The predetermined fraction is empirically determined. This embodiment of the analysis is less sensitive to variation of the backscattered intensity due to variations of the transmission of the various sections of the eye from patient to patient.

Laser-treated tissue is identified and the laser treatment process is controlled in accordance with the present invention as follows. Data from a transverse plane are obtained during pulses of treatment laser 680 and the data are stored in computer 670. A typical transverse plane includes an area of about 2 mm by 1 mm and a typical set of data for the typical transverse plane includes data from a grid of about 30 by 100 values. The length of a typical laser pulse used in treatment is about 100 ms. In accordance with a preferred embodiment of the present invention, up to ten (10) OCT scan data sets are acquired during the 100 ms laser pulse. This means that data from each transverse plane (comprised of 3000 values) has to be processed in 10 ms. In the preferred embodiment, in analyzing the amplitude data for a transverse plane, if the amplitude at a location in the grid is higher than the reference threshold level, it is assumed that grid location corresponds to laser-treated tissue. As the data for each location in the grid is analyzed, an entry is made in a matrix corresponding to the location in the grid of laser-treated tissue and a counter is increased by one step for each location at which laser-treated tissue is detected. The counter counts the number of grid locations in the transverse plane where the effects of laser treatment are measurable. The process is completed after a full OCT data set for the transverse plane comprising 30 by 100 data values has been acquired. The final counter value gives a measure of the laser treated area of the transverse plane. In a further embodiment of the present invention, the data for the grid is imaged on the display in such a manner that grid locations which have been determined to show the effects of laser treatment are identified. For example, the values which exceed the reference threshold may be displayed in a different color from that of surrounding tissue. This provides a visual picture of the effects of the laser treatment over the transverse plane for the operator.

In the embodiment described above, it is advantageous to analyze the data from a transverse plane to save processing time. This advantage occurs when using a symmetrical laser beam so that the effect of the laser treatment is symmetrical about a line along the longitudinal direction into eye 1000. However, the present invention includes embodiments which detect laser-treated tissue over a volume. In accordance with the present invention, data for a volume of eye 1000 is obtained by rotating the direction of the linear, transverse OCT scan by a predetermined amount in the manner described above, i.e., by varying the ratio of the amplitudes of the sawtooth voltages applied to drive scanning mirrors 850 and 860. Then, data are collected for the plane at the rotated position, the plane is rotated again, and so forth, until data is collected for the volume. The data are analyzed in the manner described above to provide a matrix which identifies laser-treated tissue. In addition, counters for all of the transverse planes are summed to provide a measure of the laser-treated volume. In the further embodiment, the volume is imaged on the display in such a manner that locations which have been determined to show the effects of laser treatment are identified. For example, the values which exceed the reference threshold may be displayed in a different color from the that of surrounding tissue. This provides a visual picture of the effects of the laser treatment over the volume.

In accordance with the present invention, the measured area of a transverse plane of laser-treated tissue is used to control one or more of the following parameters: (a) for treatment laser 670; exposure time and power and (b) for lenses 720 and 730; the spot size of treatment laser 670. As described above, the measured area of a transverse plane of laser-treated tissue is measured several times during a laser exposure and the measured areas are compared with empirically determined reference values for each of those measurements. In a preferred embodiment, the reference values are selected so that the area of the laser-treated tissue in a transverse plane is small enough to avoid damage to neighboring tissue and, in accordance with the present invention, the laser is automatically turned off before this limit value is reached. As one can readily appreciate, the exposure time and power for treatment laser 680 and the spot size of the beam may be found to depend on the difference between a measured amplitude and a reference threshold level. In such cases, empirical studies may be used to control the values of these parameters depending, not only on whether an amplitude exceeds or falls below a reference threshold level, but on the value of the difference between the amplitude and the reference threshold value. It should be clear as to fabricate embodiments of the present invention which take such effects into account in light of the above.

In further embodiments, a measured volume of laser-treated tissue is used to control one or more of the following parameters: (a) for treatment laser 670; exposure time and power and (b) for lenses 720 and 730; the spot size of treatment laser 670. In accordance with the present invention, the measured volume of laser-treated tissue is measured one or more times during and the measured volumes are compared with empirically determined reference values for each of those measurements. It should be understood that the detection of areas and/or volumes of laser-treated tissue are not limited to detection during the application of a laser pulse and that such detection may take place after the laser pulse has been applied.

Those skilled in the art will recognize that the foregoing description has been presented for the sake of illustration and description only. As such, it is not intended to be exhaustive or to limit the invention to the precise form disclosed.

What is claimed is:

1. Apparatus for determining tissues effected by laser radiation that remain in an object that has been exposed to the laser radiation, which apparatus comprises:

an optical coherence tomography (OCT) apparatus;

a scanner which: (a) scans the object with radiation output from the OCT apparatus and (b) couples radiation backscattered from tissues remaining in the object into the OCT apparatus;

the OCT apparatus comprising a detector, in response to the backscattered radiation, which outputs detection signals; and an analyzer which analyzes the detection signals output from the OCT apparatus to determine measures of amplitude of the backscattered radiation to produce an output which indicates tissues remaining in the object whose properties of interaction with the radiation have been effected by the laser radiation.

2. Apparatus for applying laser radiation to an object and identifying tissues remaining in the object whose properties of interaction with the radiation have been effected by the laser radiation, which apparatus comprises:

a controller;

a laser which outputs laser radiation in response to input from the controller;

a laser delivery system which applies the laser radiation to the object;

an optical coherence tomography (OCT) apparatus;

a scanner which, in response to input from the controller:
(a) scans the object with radiation output from the OCT apparatus and (b) couples radiation backscattered from tissues remaining in the object into the OCT apparatus;

the OCT apparatus comprising a detector, in response to the backscattered radiation, which outputs detection signals;

an analyzer which analyzes the detection signals output from the OCT apparatus to produce an output which indicates tissues remaining in the object whose properties of interaction with the radiation have been effected by the laser radiation; and a display device which, in response to the output from the analyzer, displays the tissues.

3. The apparatus of claim 2, wherein the tissues remaining in the object whose properties of interaction with the radiation have been effected by the laser radiation are displayed in a color which is different from that of surrounding tissue.

4. Apparatus for applying laser radiation to an object, determining tissues remaining in the object whose properties of interaction with the radiation have been effected by the laser radiation, and affecting the laser radiation applied to the object, which apparatus comprises:

a laser for producing laser radiation in response to signals from a laser control unit;

a laser delivery system for applying the laser radiation to the object;

an optical coherence tomography (OCT) apparatus;

a scanner which: (a) scans the object with radiation output from the OCT apparatus and (b) couples radiation backscattered from tissues remaining in the object into the OCT apparatus;

the OCT apparatus comprising a detector, in response to the backscattered radiation, which outputs detection signals; and an analyzer which: (a) analyzes the detection signals output from the OCT apparatus to produce an output which indicates tissues remaining in the object whose properties of interaction with the radiation have been effected by the laser radiation and, in response to the output, (b) produces a further output which is applied as input to one or more of: (a) the laser control unit and (b) the laser delivery system to set one or more of: (a) an exposure time, (b) a power, and (c) a spot size of the laser radiation.

5. The apparatus of claim 4 wherein the scanner comprises a radiation system which produces principal rays of the radiation output from the OCT apparatus in the same plane as the laser radiation emerging from the laser delivery system.

6. The apparatus of claim 5 wherein the principal rays and the laser radiation are focused through a lens system, whereby the principal rays are scanned symmetrically across a focus of the laser radiation.

7. The apparatus of claim 4 which further comprises an applicator which combines and directs the laser radiation output from the laser delivery system and the scanned radiation output from the scanner to the object.

8. The apparatus of claim 7 wherein the applicator comprises a micromanipulator lens which is movable in a plane and a director which directs output from the micromanipulator lens to the object.

9. The apparatus of claim 4 wherein the analyzer comprises a comparator which compares measures of the detection signals output from the OCT apparatus with reference threshold levels.

10. The apparatus of claim 9 wherein the analyzer further comprises an identifier which indicates the tissues remaining in the object as being disposed in one or more of: (a) transverse planes disposed in the object and (b) volumes disposed in the object.

11. The apparatus of claim 9 wherein the comparator comprises a counter which counts a number of instances in which measures of amplitude of the detection signals exceed the reference threshold levels for one or more areas of transverse planes disposed in the object and which compares the number for the one or more areas with stored data.

12. The apparatus of claim 9 wherein the analyzer produces an output when the comparator determines that measures of amplitude of the detection signals exceed the reference threshold levels.

13. The apparatus of claim 4 wherein the laser delivery system comprises a parfocal optical system.

14. The apparatus of claim 13 wherein the parfocal optical system comprises a positioner which causes changes in the laser spot size by changing positions of optical elements which comprise the parfocal optical system.

15. The apparatus of claim 14 wherein the optical elements of the parfocal optical system comprise a converging lens system and a diverging lens system and the positioner changes relative positions of the lens systems along an axis of the parfocal optical system.

16. The apparatus of claim 4 wherein the scanner comprises orthogonally mounted mirrors and a computer directed mirror driver which drives the mirrors.

17. The apparatus of claim 16 wherein the computer directed mirror driver comprises a voltage driver which applies sawtooth-profiled voltage functions to motors on which each of the mirrors is mounted.

18. The apparatus of claim 17 wherein the voltage driver includes a phase and frequency adjuster which adjusts a phase and frequency of the voltage functions to produce a linear scan of the radiation output from the OCT apparatus.

19. The apparatus of claim 18 wherein the computer directed mirror driver causes the voltage driver to adjust the phase and frequency of the voltage functions at specific times and the OCT apparatus produces a longitudinal scan into the object at the specific times to produce an OCT scan in a transverse plane in the object.

20. The apparatus of claim 19 wherein the voltage driver further includes an amplitude adjuster which adjusts amplitudes of the voltage functions to adjust an orientation of the linear scan and, thereby, the orientation of the transverse plane.

21. The apparatus of claim 20 wherein the scanner and the laser delivery system are disposed so that principal rays of the radiation output from the scanner are in a plane and the laser radiation emerging from the laser delivery system is in the plane.

22. The apparatus of claim 21 which further comprises an applicator which combines and directs the laser radiation and the scanned radiation to the object.

23. The apparatus of claim 4 wherein the analyzer comprises a comparator which determines measures of amplitude of the backscattered radiation and which compares the amplitude measures with one or more reference threshold levels.

24. The apparatus of claim 23 wherein the comparator compares the measures of amplitude with multiple valued reference threshold levels that are functions of one or more of laser power, exposure time, and tissue type of the object.

25. The apparatus of claim 23 wherein the analyzer, in response to input from the comparator, produces the output which indicates that tissue in the object that backscatters radiation with an amplitude measure (a) above the one or more reference threshold levels has had it's properties of interaction with the radiation effected by the laser radiation and (b) below the one or more reference threshold levels has not had it's properties of interaction with the radiation effected by the laser radiation.

26. The apparatus of claim 23 wherein the analyzer comprises a scanner director which sends signals to cause the scanner to produce a linear scan of the radiation and, the analyzer further comprises a detection signal collector which collects, at predetermined points in the linear scan, amplitude measures of the backscattered radiation at a multiplicity of positions of depth along a longitudinal direction into the object, thereby obtaining amplitude measures over a transverse plane in the object.

27. The apparatus of claim 26 which further comprises a radiation combiner which combines the laser radiation and the scanned radiation so that the linear scan extends substantially symmetrically about a focus of the laser radiation on the object.

28. The apparatus of claim 27 wherein the analyzer determines an area of tissue whose properties of interaction with the radiation has been effected by the laser radiation in the transverse plane.

29. The apparatus of claim 28 wherein the analyzer determines the area of tissue whose properties of interaction with radiation has been effected by the laser radiation one or more times during a laser pulse.

30. The apparatus of claim 28 wherein the analyzer compares the area of tissue whose properties of interaction with the radiation has been effected by the laser radiation with a predetermined reference area to determine whether to provide further laser exposure.

31. The apparatus of claim 30 wherein the analyzer sends the further output to the laser control unit to cause the laser control unit to turn off the laser or to change the exposure time.

32. The apparatus of claim 30 wherein the analyzer sends the further output to the laser delivery system to change the laser spot size.

33. The apparatus of claim 32 wherein the laser delivery system includes movable lenses for altering the laser spot size and the analyzer further includes a laser delivery system analysis system which determines and displays positions of the lenses that will provide a desired spot size.

34. The apparatus of claim 28 wherein the analyzer determines the area by comparing the amplitude measures with one or more reference threshold levels.

35. The apparatus of claim 34 wherein the analyzer includes a level tester which determines whether the amplitude measures exceed or fall below the one or more reference threshold levels and the value of the difference between the amplitude measures and the one or more reference threshold levels.

36. The apparatus of claim 34 wherein the analyzer determines the area one or more times during a laser pulse.

37. The apparatus of claim 34 wherein the analyzer determines the area after a laser pulse.

38. The apparatus of claim 34 wherein the analyzer comprises an area tester which determines the area by entering a notation in a matrix corresponding to a location in the transverse plane of tissue whose properties of interaction with the radiation has been effected by the laser radiation and increasing a counter by one step for each location at which tissue whose properties of interaction with the radiation has been effected by the laser radiation is detected, wherein a final counter value provides a measure of tissue whose properties of interaction with the radiation has been effected by the laser radiation in the transverse plane.

39. The apparatus of claim 26 wherein the scanner director includes a rotator director which sends further signals to cause the scanner to rotate the direction of the linear scan of radiation by a predetermined number of predetermined amounts and wherein the detection signal collector further comprises a rotation detection signal collector which collects amplitude measures of the backscattered radiation for the transverse planes at each of the rotated positions, thereby obtaining amplitude measures in a volume in the object.

40. The apparatus of claim 39 wherein the analyzer determines a volume of tissue whose properties of interaction with radiation has been effected by the laser radiation in the volume.

41. The apparatus of claim 40 wherein the analyzer determines the volume of tissue whose properties of interaction with the radiation has been effected by the laser radiation one or more times during a laser pulse.

42. The apparatus of claim 40 wherein the analyzer determines the volume by comparing the amplitude measures with one or more reference threshold levels.

43. The apparatus of claim 42 wherein the analyzer includes a level tester which determines whether the amplitude measures exceed or fall below the one or more reference threshold levels and on the value of the difference between the amplitude measures and the one or more reference threshold levels.

44. The apparatus of claim 42 wherein the analyzer determines the volume one or more times during a laser pulse.

45. The apparatus of claim 42 wherein the analyzer determines the volume after a laser pulse.

46. The apparatus of claim 42 wherein the analyzer comprises a volume tester which determines the volume by, for each of the transverse planes, entering a notation in a matrix corresponding to a location in the transverse plane of tissue whose properties of interaction with the radiation has been effected by the laser radiation and increasing a counter by one step for each location at which tissue whose properties of interaction with the radiation has been effected by the laser radiation is detected, wherein a final counter value provides a measure of tissue whose properties of interaction with the radiation has been effected by the laser radiation in the transverse plane, and by summing counters for all of the transverse planes to provide a measure of tissue whose properties of interaction with the radiation has been effected by the laser radiation in the volume.

47. The apparatus of claim 40 wherein the analyzer compares the volume of tissue whose properties of interaction with the radiation has been effected by the laser radiation with a predetermined reference volume to determine whether to provide further laser exposure.

48. The apparatus of claim 47 wherein the analyzer sends the further output to the laser control unit to cause the laser control unit to turn off the laser or to change the exposure time.

49. The apparatus of claim 48 wherein the analyzer sends the further output to the laser delivery system to change the laser spot size.

* * * * *